US00PP32076P2

(12) United States Plant Patent
Lowe

(10) Patent No.: US PP32,076 P2
(45) Date of Patent: Aug. 18, 2020

(54) KIWIFRUIT PLANT NAMED 'ZES008'

(50) Latin Name: ***Actinidia chinensis* var. *chinensis***
Varietal Denomination: ZES008

(71) Applicant: Zespri Group Limited, Mount Maunganui (NZ)

(72) Inventor: Russell Lowe, Te Puke (NZ)

(73) Assignee: ZESPRI GROUP LIMITED, Mount Maunganui (NZ)

( * ) Notice: Subject to any disclaimer, the term of this patent is extended or adjusted under 35 U.S.C. 154(b) by 0 days.

(21) Appl. No.: 16/501,576

(22) Filed: May 2, 2019

(51) Int. Cl.
*A01H 5/08* (2018.01)

(52) U.S. Cl.
USPC ..... Plt./156

(58) Field of Classification Search
USPC ..... Plt./156
CPC ..... A01H 5/08
See application file for complete search history.

(56) References Cited

U.S. PATENT DOCUMENTS

PP20,893 P3 3/2010 Lowe et al.
PP21,613 P3 1/2011 Lowe et al.

*Primary Examiner* — Annette H Para
(74) *Attorney, Agent, or Firm* — Baker & McKenzie LLP

(57) ABSTRACT

A new, distinct, and stable variety of the plant *Actinidia chinensis* var. *chinensis* is disclosed. The variety of plant results from the selection among a population of seedlings derived from crossing the kiwifruit selections known as 'ZES006' and CK51_09 (unpatented). The variety of plant is characterized by a medium-weight, high sweetness fruit with a dark, very strong spread of reddish color along the locules. The new variety of plant has been named 'ZES008'.

4 Drawing Sheets

Latin name of the genus and species of the plant claimed: *Actinidia chinensis* var. *chinensis.*

Variety denomination: 'ZES008'.

BACKGROUND AND SUMMARY OF THE DISCLOSURE

The disclosure relates to the discovery and asexual propagation of a new and distinct variety of the kiwifruit plant, *Actinidia chinensis* var. *chinensis* 'ZES008', as herein described and illustrated. The new kiwifruit plant variety 'ZES008' was selected from a population of seedlings derived from crossing two kiwifruit selections: *A. chinensis* female 'ZES006' x *A. chinensis* male CK51_09 (unpatented) by controlled pollination and as part of a large breeding program. The cross was made in October 2005 at Te Puke, Bay of Plenty, New Zealand. The variety was selected as K07.19-10-09e and has been named 'ZES008'. It was selected for its high sweetness and consistently dark, very strong spread of reddish color along the locules.

BRIEF DESCRIPTION OF THE DRAWINGS

The accompanying photographs show typical specimens in full color of the fruit, flowers, and leaves of the new variety 'ZES008'. Plants were observed beginning in 2011. The colors as depicted are as nearly true as is reasonably possible in a color representation of this type. Colors may vary depending upon growing conditions under different climate, soil, and cultivation conditions. Fruit skin color may also vary depending upon extent of exposure to direct sunlight.

The file of this patent contains at least one drawing executed in color. Copies of this patent with color drawing(s) will be provided by the Patent and Trademark Office upon request and payment of the necessary fee.

Figure 1:
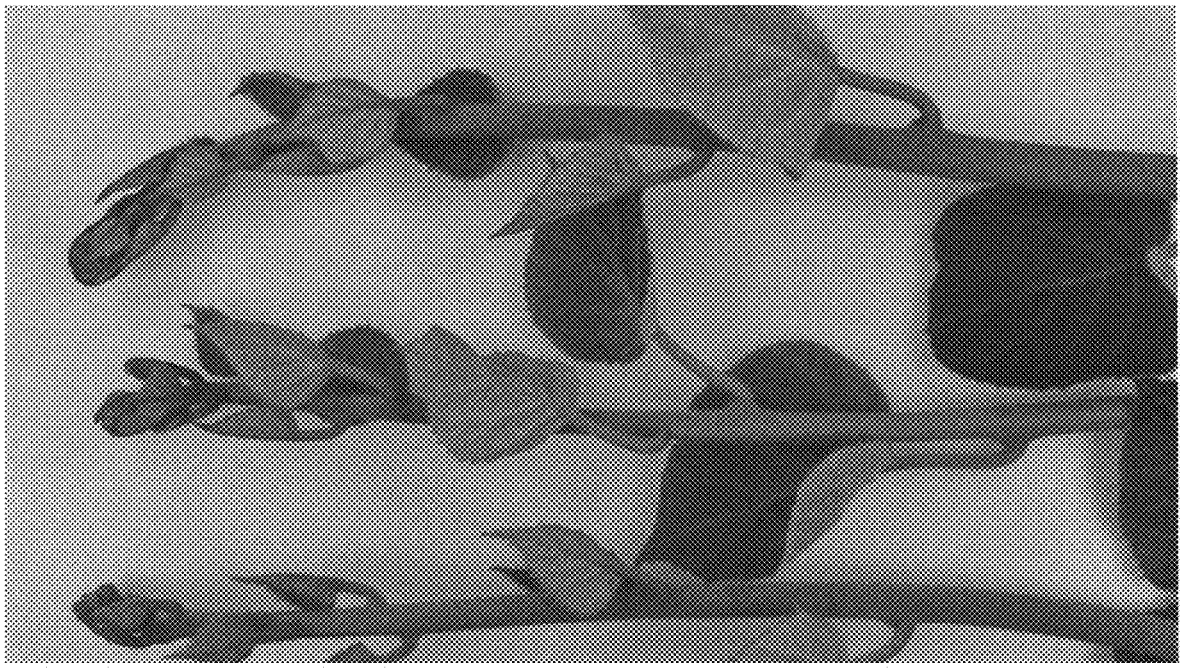
Figure 2:
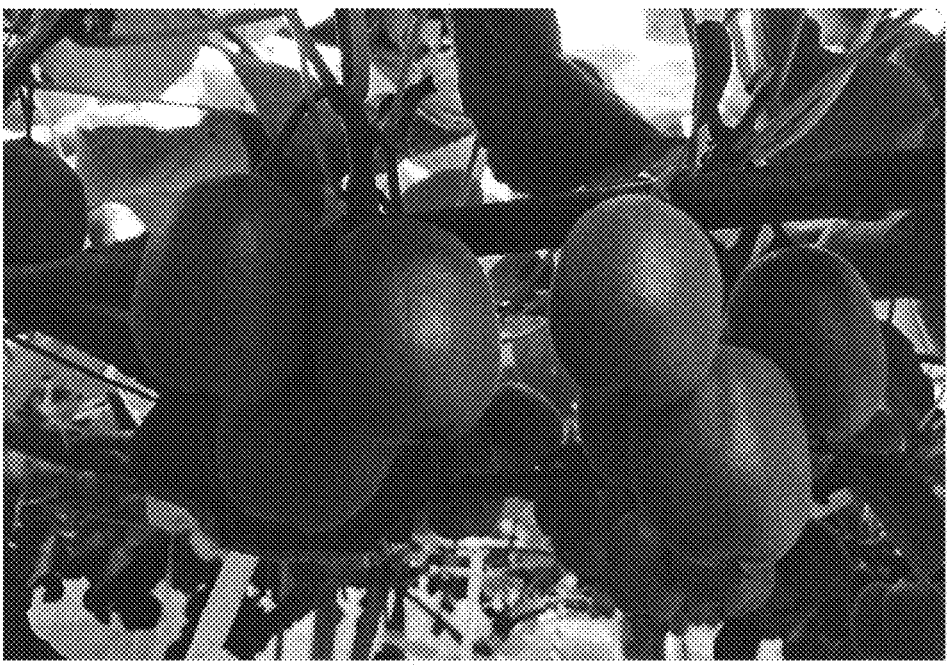
Figure 3:
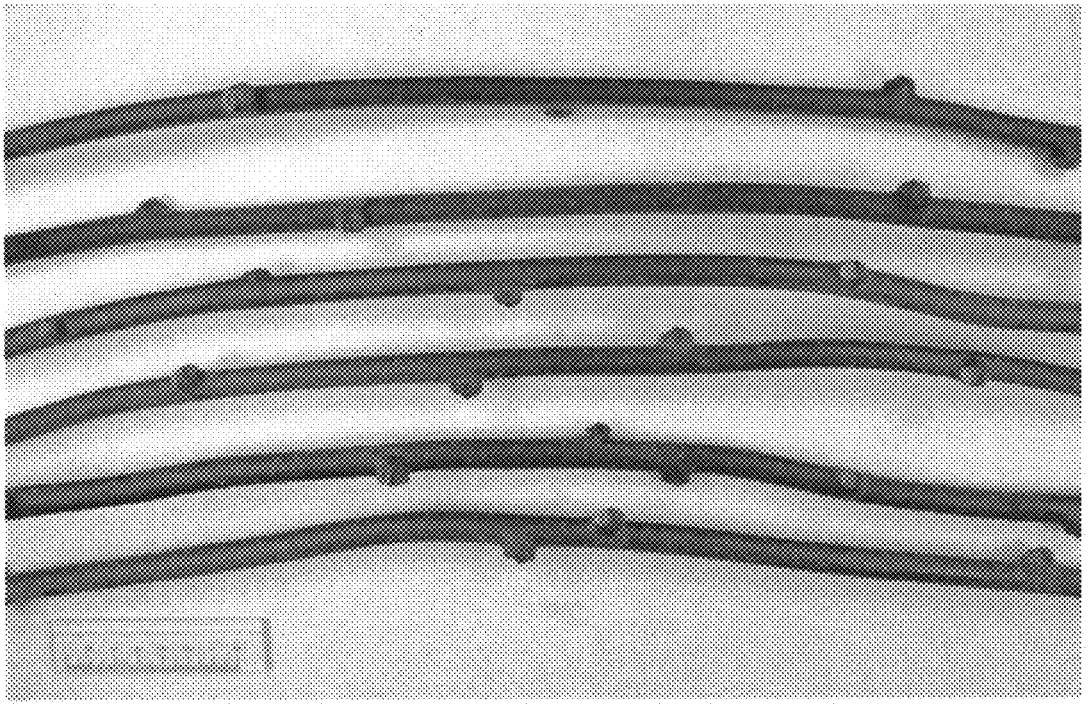
Figure 4:
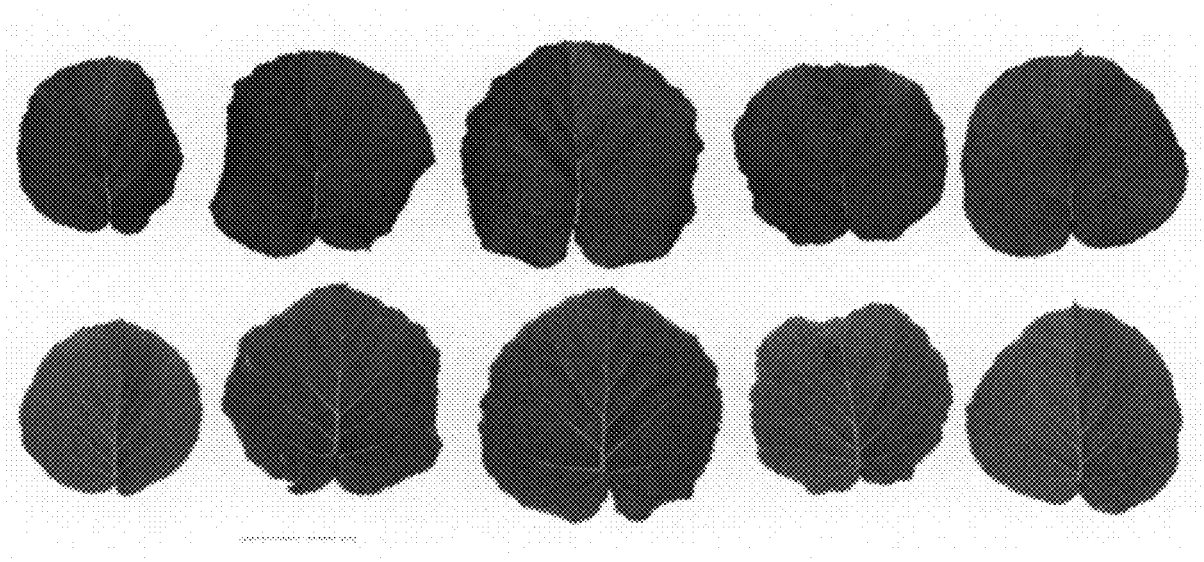
Figure 5:
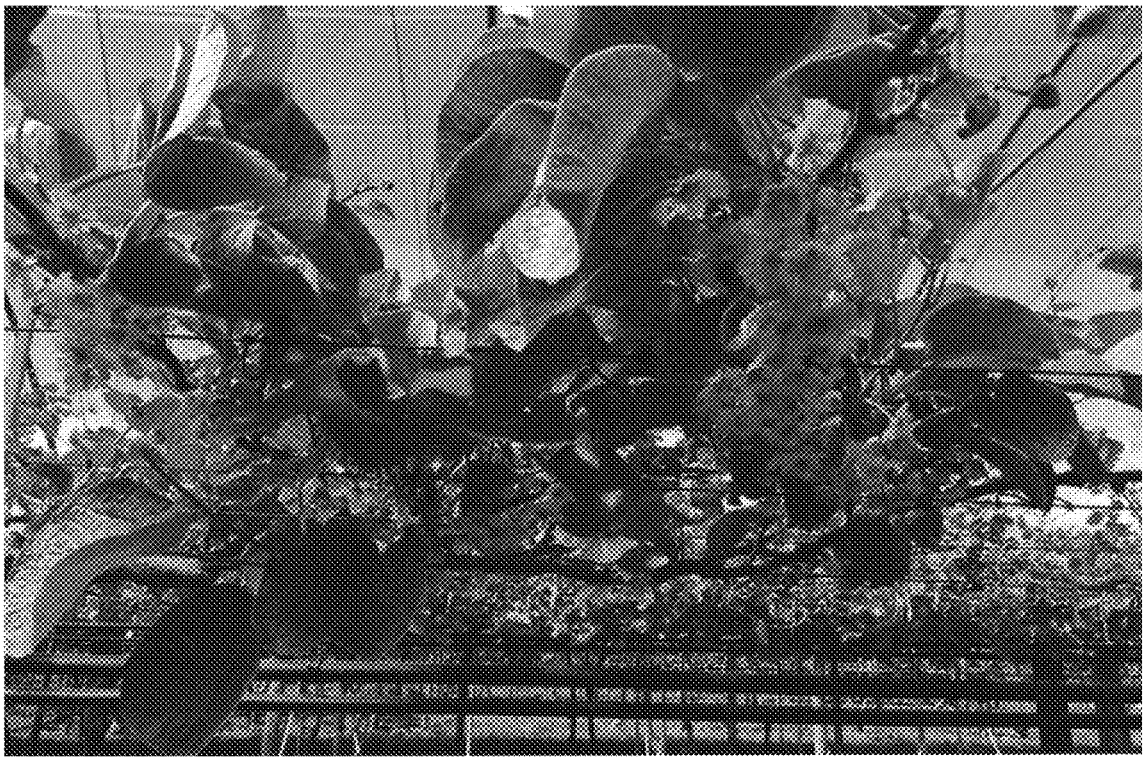
Figure 6:
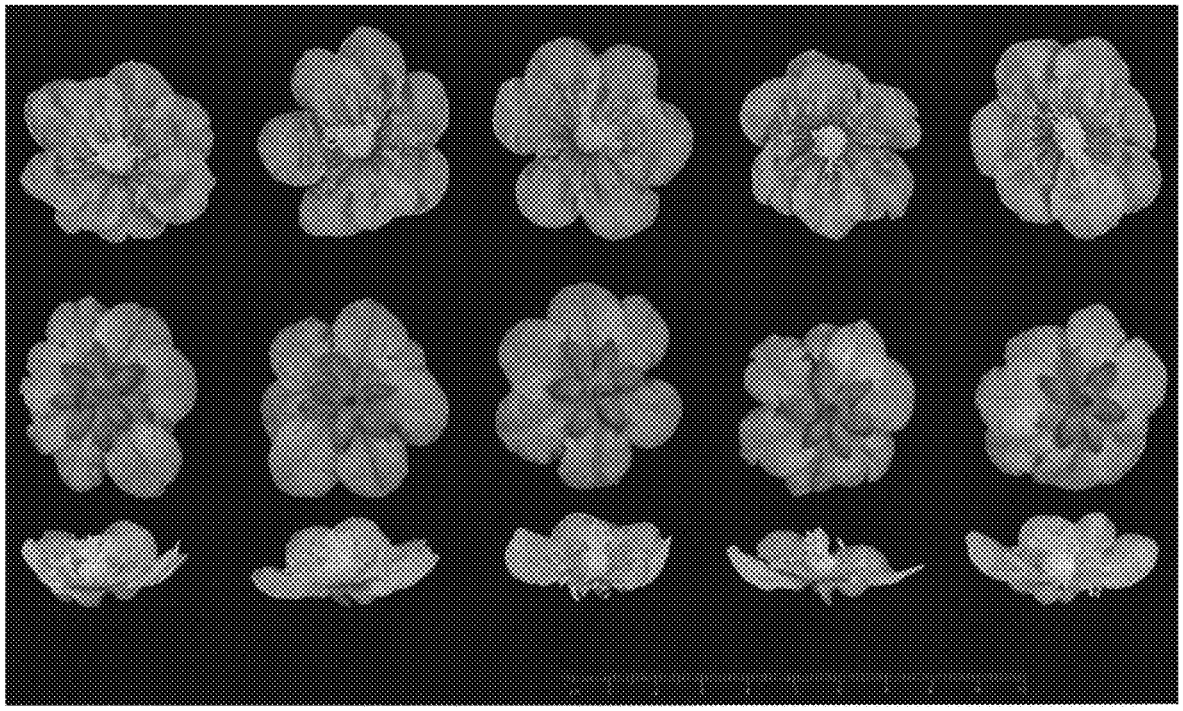
Figure 7:
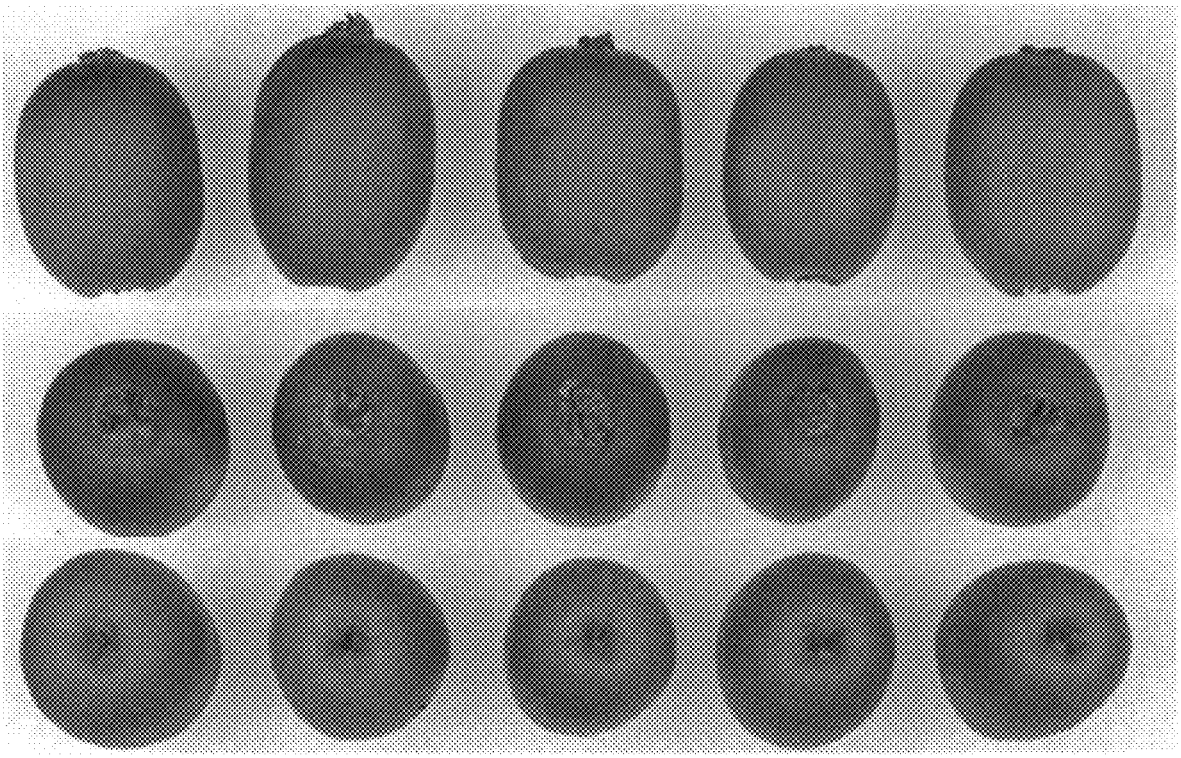
Figure 8:
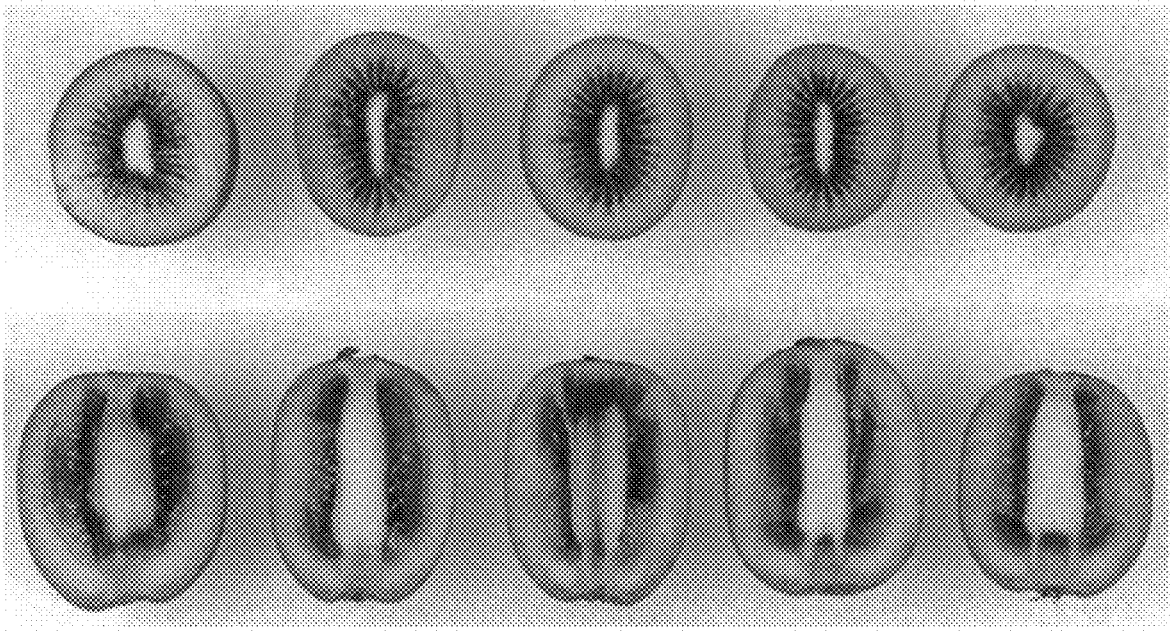

Some embodiments of the disclosure may be understood by referring, in part, to the present disclosure and the accompanying photographs, wherein:

FIG. 1 illustrates typical young shoots of the disclosed variety 'ZES008' according to a specific embodiment of the disclosure;

FIG. 2 illustrates typical fruit (on the vine), stems, and leaves of the disclosed variety 'ZES008' according to a specific example embodiment of the disclosure;

FIG. 3 illustrates typical dormant, one-year-old stems of the disclosed variety 'ZES008' according to a specific example embodiment of the disclosure;

FIG. 4 illustrates the adaxial (top) surface (top row) and abaxial (bottom) surface (bottom row) of typical mature leaves of the disclosed variety 'ZES008' according to a specific example embodiment of the disclosure;

FIG. 5 illustrates typical flowers (on the vine) and leaves of the disclosed variety 'ZES008' according to a specific example embodiment of the disclosure;

FIG. 6 illustrates a top view (top row), bottom view (middle row), and side view (bottom row) of typical flowers (in the studio) of the disclosed variety 'ZES008' according to a specific example embodiment of the disclosure;

FIG. 7 illustrates typical fruit (in the studio) of the disclosed variety 'ZES008' from a side-view (top row), a top-view (middle row), and a bottom-view (bottom row) according to a specific example embodiment of the disclosure; and FIG. 8 illustrates a typical fruit of the disclosed variety 'ZES008' in cross-section (top row) and longitudinal-section (bottom row) according to a specific example embodiment of the disclosure.

DETAILED DESCRIPTION

The following is a detailed description of the new plant variety. The specimens described were grown, asexually propagated, and observed in New Zealand at The New Zealand Institute for Plant and Food Research Limited, which is located across multiple regions including Northland, Bay of Plenty, and Gisborne. Vines of 'ZES008' were grafted onto existing 'Bruno' rootstock and grown in replicated plots alongside comparison varieties.

All varieties discussed and described herein were managed under standard orchard practice. This included growing the plants on a standard pergola structure at a height of 1.8 m, and allowing each plant to canopy an area of approximately 15 $m^2$. Except where otherwise noted, measurements of each characteristic were obtained from ten randomly selected plants.

All dimensions are in millimeters and all weights are in grams (unless otherwise stated). Certain characteristics of this variety and the comparison varieties discussed herein, such as growth and color, may change with changing environmental conditions (e.g., light, temperature, moisture), nutrient availability, rootstocks, or other factors. Color descriptions and other terminology are used in accordance with their ordinary dictionary descriptions, unless the context clearly indicates otherwise. Color names beginning with a capital letter designate values based upon The R.H.S. Colour Chart published by The Royal Horticultural Society, London, England (2001 Edition).

BOTANICAL DESCRIPTION OF THE PLANT

The new plant variety, 'ZES008' is described in detail below based upon growth trials performed in New Zealand. Traditional fruit breeding methodology was used to develop new kiwifruit varieties as part of a large breeding program. In October of 2005, 'ZES008' was bred by hybridization through the controlled pollination of female plants of the variety 'ZES006' with male pollen of the variety CK51_09. In July 2011, seedlings (progeny plants) were selected based on project criteria for characteristics such as high sweetness and consistently dark, very strong spread of reddish color along the locules. In 2011, the selected progeny were asexually propagated and grafted onto 'Bruno' rootstock for further evaluation and selection (replicated clonal trials). Other rootstocks sources may be used without varying from this disclosure. The replicated clonal trials were evaluated between 2011 and 2019 for uniformity and stability. Asexual propagation of the new kiwifruit variety 'ZES008' by grafting shows that the unique combination of characteristics of the variety come true to form and are established and transmitted through succeeding propagation. To obtain true-to-type clones of the initial plants, asexually propagated plants were obtained by grafting dormant buds from the original seedlings onto rootstocks. Scions were grafted in the winter months and were analyzed and described during their second and third years of fruiting.

Male pollen parent CK51_09 was bred by The New Zealand Institute for Plant and Food Research. The male pollen parent is distinguishable from 'ZES008' at least in that it does not bear fruit.

Female parent 'ZES006' was also bred by The New Zealand Institute for Plant and Food Research. The female parent is distinguishable from 'ZES008' at least in that it has: a more depressed leaf scar; a sparser density of hairs on the petiole; shorter hair on the flower stalk; an elliptic general fruit shape; a weakly sloping shoulder shape at the stalk end; an orange-white fruit core color at harvest; a medium adherence of fruit skin to fruit flesh at eating ripeness; an oblate fruit core in cross section; and high sweetness. The variety 'ZES008' is maintained by vegetative propagation through cutting, propagation, and grafting. Suitable male pollinizers for the candidate variety include 'Bruce' (U.S. Plant Pat. No. 21,613) and 'Sparkler'.

PLANT AND FOLIAGE

The disclosed variety is a female plant that is diploid and lacks self-setting (absent). It expresses an upright and spreading habit and readily grows on a string canopy structure. It is moderate in size and has medium vigor.

Young shoots (FIG. 1) of 'ZES008' exhibit sparse tomentose hairs. The anthocyanin (red) coloration on the growing tips of the young shoots is absent or very weak (RHS 146C) and the anthocyanin (red) coloration of the leaf axil is also absent or very weak (RHS 152D).

Dormant one-year-old stems (FIG. 2, FIG. 3) of 'ZES008' have red-brown (RHS 166A) coloring on the upper side. On average, dormant one-year-old stems have 5.1 lenticels per $cm^2$ (range 3 to 7) (few), with the lenticels being medium in size and having a brown color (RHS 165D). The average diameter of one-year-old stems is 11.3 mm (range 9.8 mm to 12.4 mm) (medium), based on a 20-stem sample. One-year-old stems typically have very little waxy white powder on the surface of their smooth bark. The one year-old stems have absent or sparse hairs that are downy in texture.

The average dormant bud diameter is 6.7 mm (range 5 mm to 8.9 mm), based on a sample size of 20 stems. Prominence of bud support is medium and the proximal face of the bud support is perpendicular. The leaf scar of one-year-old stems is strongly depressed. The pith is lamellate. The mark of the petiole is moderate in depth.

The leaf blade of 'ZES008' is broad ovate in shape, medium in size, with an acuminate-shaped leaf tip (FIG. 4, FIG. 5). The ratio of length to width of the leaf blade is intermediate. The green coloration on the upper surface of a typical 'ZES008' leaf blade is moderate in its intensity (RHS 147A) (FIG. 4 top row), while the lower surface of the leaves are yellow green (RHS 147B) in color (FIG. 4 bottom row). The variety includes both leaves on which basal lobes are slightly apart and leaves on which the basal lobes touch (touching each other). Typically the leaves are not variegated (absent). The number of ciliate serrations on the leaf blade of 'ZES008' is few and those serrations that are present are small in size. The upper side of the leaf has only sparse hairs if any, while the lower side of the leaf is covered by a moderately dense covering of hairs (medium). There is weak puckering/blistering on the upper side of the leaf blade.

The petiole of 'ZES008' is medium to large relative to the leaf blade, with the average length of a petiole being 105.3 mm (range 84 mm to 128 mm), based on 20 samples. The upper side of the 'ZES008' petioles have only weak anthocyanin (red) coloration (RHS 59B).

INFLORESCENCE

Characteristics of 'ZES008' inflorescence were calculated based on the results of a 20-flower sample. The inflorescence (FIG. 5) of 'ZES008' is solitary and, on average, many flowers are present in each inflorescence. There is an average of 5.4 inflorescences per lateral shoot (range 4 to 6), 0.8 lateral flowers per shoot (range 0 to 3), and 0.1 lateral flowers per inflorescence (range 0 to 0.5). Anthocyanin (red) color is absent to very weak on the unopened flower, with red coloration (RHS N66A) on the calyx edges. The position of the first spike on the flower bud is low and the protruding petal end has very weak anthocyanin (red) coloration. The flower stalk is short in length and has a moderate density of medium length hair. The basal node is spike bearing.

'ZES008' flowers typically have an average of 7.4 sepals (range 6 to 10 sepals), which are green (RHS 138B) with a medium density of short sepal hairs. Terminal flowers of 'ZES008' are, on average, 44.9 mm in diameter (range 40.7 mm to 50.1 mm) (medium) with overlapping petals. Flowers have a concave shape in profile and a moderate petal shoulder (FIG. 6). Each flower of 'ZES008' has a medium number of petals with the average being 7.8 petals (range 6 to 9) per flower, and with 80% of the flowers having more than 6 petals. Petals have an average length of 21.8 mm (range 19.7 mm to 23.9 mm), an average width of 17.7 mm (range 14.7 mm to 21.5 mm), and an average petal length/width ratio of 1.2 (range 1 to 1.4). Petals are yellowish white in color on the adaxial side (RHS 158C) with even shading of the main color, and green secondary coloration which is distributed as a basal spot only. The petal apex is weakly curved upwards, and both the petal base and the filament are light green in color.

Each flower typically has about 33.8 styles (range 30 to 40) (medium), the styles having an irregular attitude, a weak sinosity, and white color. The average peduncle length is 46.4 mm (range 33.5 mm to 57.6 mm). There are a medium number of anthers that are yellow orange in color (RHS 20A). Ovaries are ovoid in shape.

FRUIT

The 'ZES008' plant produces a fruit that is elliptic in shape (FIG. 2, FIG. 7) and oblate in shape at cross section (FIG. 8, top row). The maximum lateral diameter of the fruit is in the equatorial portion of the fruit. The fruit has an average length of 60 mm (range 57 mm to 62.6 mm) (short), a narrow-medium width, and a medium length to width ratio. The maximum diameter of the fruit on average is 45.9 mm (range 42.5 mm to 49.9 mm) and the minimum diameter is on average 42.9 mm (range 39.8 mm to 46.2 mm), making the ratio of maximum to minimum diameter 1.1. 'ZES008' produces fruit with medium weight, averaging around 73.5 g (range 62.3 g to 87 g).

'ZES008' fruit has a weakly depressed stylar end. The calyx ring of the fruit is medium expressed.

The stalk of 'ZES008' fruit has a medium thickness and is short in length, averaging 35.4 mm (range 26.5 mm to 49.7 mm). The stalk length to fruit length ratio is 0.6 (range 0.4 to 0.9) (medium). The fruit shoulder at the stalk end is weakly sloping.

'ZES008' fruit has greenish brown skin (RHS 152A at harvest, RHS 152C at eating maturity) that moderately adheres to the flesh of the fruit at eating ripeness (medium). The small, but numerous, lenticels on the skin have medium conspicuousness. The fruit of 'ZES008' is hairy, having a medium density of reddish-brown colored hairs (RHS 163B). The downy hairs are primarily found at the stylar end of the fruit and are short, soft, and weakly adhere to the skin of the 'ZES008' fruit. 'ZES008' fruit has a persistent sepal.

The average core diameter of 'ZES008' fruit is 10.7 mm (range 8.6 mm to 12.4 mm), with an average minimum core diameter of 7.3 mm (range 5 mm to 10.4 mm) and an average maximum core diameter of 14.1 mm (range 10.4 mm to 19.2 mm). The fruit core has a medium width relative to the 'ZES008' fruit. The fruit core is orange-white (RHS 159B) in color at harvest and is white in color (RHS 155A) at eating ripeness. In cross-section the 'ZES008' fruit core is oblate in shape (FIG. 8, top row).

At eating ripeness, the outer pericarp of 'ZES008' is greenish-yellow in color with red speckles (RHS 46A) with substantial variation in the amount of speckling from fruit to fruit. The fruit has, on average, about 31.7 locules (range 29 to 35), which are red (RHS 46A) and dark. The spread of reddish color along the locules is very strong (FIG. 8).

'ZES008' fruit has a high sweetness value with an average ripe brix value of 21.1 (range 18.7 to 23.9).

TIMING OF HORTICULTURAL EVENTS

'ZES008' plants display an early timing of vegetative bud burst (10% of buds showing green shoots) with budbreak occurring in early September in New Zealand.

The beginning of flowering time (10% of flowers being fully opened) for 'ZES008' plants is early, occurring in mid-October in New Zealand. The timing of fruit maturity for harvest of 'ZES008' plants is early with fruit harvest in New Zealand beginning in late March. Fruit harvested at a commercially appropriate firmness of 4-7 kgf between late March and early April in New Zealand required a period of ripening before they were soft enough to eat. The fruit is capable of maintaining a mean firmness above 0.5 kgf for up to twenty weeks under suitable conditions (e.g., cold storage with a controlled atmospheric environment having increased $CO_2$ levels and low $O_2$).

CULTIVATION

'ZES008' is maintained as grafted plants in an orchard setting in the Te Puke region of New Zealand by appropriate personnel at the New Zealand Institute for Plant and Food Research. The typical rootstock for 'ZES008' is 'Bruno', however 'ZES008' plants can be grown on the same rootstocks as other standard varieties (e.g., 'Hayward' and 'Hort16').

In the Southern hemisphere, seeding may be performed throughout the month of April. Planting may be performed in the Southern hemisphere from the beginning of July through the beginning of August. Grafting may be performed in the Southern hemisphere from the middle of June through the end of August. Cutting may be performed in the Southern hemisphere from the beginning of June through the end of July.

DISEASE TOLERANCE

'ZES008' appears to have substantial tolerance against bacterial flower rot caused by *Pseudomonas syringae* pv. *actinidiae* (Psa) with less than 5% of flowers being infected in the New Zealand trials.

COMPARISON TO PARENTAL VARIETIES

The distinctive characteristics of this variety, 'ZES008', described above in detail, were observed in several growing regions of New Zealand, including Northland, Bay of Plenty, and Gisborne, and in the Te Puke region of New Zealand at the New Zealand Institute for Plant and Food Research. Maternal parent variety 'ZES006' was grown in another block of the same orchard. Variations noted in TABLE 1 below between 'ZES008' and the maternal parent 'ZES006' are for example purposes only and should not be construed as the only variations between the varieties. Other variations between 'ZES008' and the parental varieties may exist. Male parent variety CK51_09 does not bear fruit.

TABLE 1

| CHARACTERISTIC | ZES008 | ZES006 |
|---|---|---|
| Stem: leaf scar | strongly depressed | moderate depressed |
| Petiole: density of hairs | sparse | moderate |
| Flower stalk: length of hair | medium | long |
| Fruit: general shape | elliptic | oblong |
| Fruit: shape of shoulder at stalk end | weakly sloping | truncate |
| Fruit: core color at harvest | orange-white | yellow-white |
| Fruit: adherence of skin to flesh at eating ripeness | medium | strong |
| Ripe fruit: general core shape in cross section | oblate | transverse elliptic |
| Ripe fruit: sweetness | high | medium |

COMPARISON TO CLOSEST CULTIVARS

The distinctive characteristics of 'ZES008', described above in detail, were observed in several growing regions of New Zealand, including Northland, Bay of Plenty, and Gisborne, and in the Te Puke region of New Zealand at the New Zealand Institute for Plant and Food Research. Comparison vines of *Actinidia chinensis* Planch cv. 'Hongyang' (hereafter 'Hongyang') were grown alongside 'ZES008' for comparison purposes. Comparison vines of *Actinidia chinensis* cv. 'Hort22D' (hereafter 'Hort22D') (U.S. Plant Pat. No. 20,893) were grown in another block of the same orchard. Variations noted in TABLE 2 below between 'ZES008', 'Hongyang', and 'Hort22D' are for example purposes only and should not be construed as the only variations between the varieties. Other variations between 'ZES008' and the noted varieties may exist.

At least 'ZES008' differs from 'Hongyang' in the degree of depression of the leaf scar, density of hairs on the petiole, length of hairs on the flower stalk, flower shape in profile, general shape of fruit, degree of depression of the stylar end of the fruit, shape of shoulder of the stalk end of the fruit, skin color at harvest, core color at harvest, adherence of skin to flesh at eating ripeness, color of outer pericarp at eating ripeness, shape of the fruit core in cross section, fruit sweetness, spread of reddish color along locules, and intensity of reddish color in locules.

At least 'ZES008' differs from 'Hort22D' in the degree of depression of the leaf scar, length of hairs on the flower stalk, general shape of fruit, degree of depression of the stylar end of the fruit, shape of shoulder of the stalk end of the fruit, skin color at harvest, density of hairs on skin, core color at harvest, adherence of skin to flesh at eating ripeness, color of outer pericarp at eating ripeness, and fruit sweetness.

The title, abstract, background, and headings are provided in compliance with regulations and/or for the convenience of the reader. They include no admissions as to the scope and content of prior art and no limitations applicable to all disclosed embodiments.

TABLE 2

| CHARACTERISTIC | ZES008 | Hongyang | Hort22D |
|---|---|---|---|
| Stem: leaf scar | strongly depressed | moderate depressed | moderate depressed |
| Petiole: density of hairs | sparse | moderate | sparse |
| Flower stalk: length of hair | medium | short | short |
| Flower: shape in profile | concave | convex | concave |
| Fruit: general shape | elliptic | oblong | oblong |
| Fruit: stylar end | weakly depressed | strongly depressed | weakly blunt protruding |
| Fruit: shape of shoulder at stalk end | weakly sloping | truncate | truncate |
| Fruit: skin color at harvest | greenish brown | yellow-green | yellow-green |
| Fruit: density of hairs on skin | medium | medium | sparse |
| Fruit: core color at harvest | orange-white | white | yellow-white |
| Fruit: adherence of skin to flesh at eating ripeness | medium | strong | strong |
| Ripe fruit: outer pericarp color at eating ripeness | yellowish-green with red speckles | yellowish-green | yellowish-green |
| Ripe fruit: general core shape in cross section | oblate | transverse elliptic | oblate/ transverse elliptic |
| Ripe fruit: sweetness | high | medium | medium |
| Ripe fruit: Average vitamin C content (mg per 100 g fruit weight) | 190.4 | 162 | 125.3 |
| Ripe fruit: spread of reddish color along locules | very strong | medium | very strong |
| Ripe fruit: intensity of reddish color in locules | dark | medium | dark |

What is claimed is:

1. A new, distinct, and stable kiwifruit plant substantially as herein described and illustrated, characterized by a medium-weight, high sweetness fruit with a dark, very strong spread of reddish color along the locules.

* * * * *